United States Patent [19]

Quarderer et al.

[11] Patent Number: 4,825,013

[45] Date of Patent: Apr. 25, 1989

[54] PREPARATION OF ETHANOL AND HIGHER ALCOHOLS FROM LOWER CARBON NUMBER ALCOHOLS

[75] Inventors: George J. Quarderer; Rex R. Stevens; Gene A. Cochran; Craig B. Murchison, all of Midland, Mich.

[73] Assignee: The Dow Chemical Company, Midland, Mich.

[21] Appl. No.: 154,536

[22] Filed: Feb. 16, 1988

Related U.S. Application Data

[63] Continuation of Ser. No. 668,598, Nov. 5, 1984, abandoned.

[51] Int. Cl.$^4$ .................. C07C 29/00; C07C 27/00; C07C 31/08; C07C 31/10
[52] U.S. Cl. ................... 568/902.2; 502/220; 518/717; 560/265
[58] Field of Search .................. 568/902 H

[56] References Cited

U.S. PATENT DOCUMENTS

| | | | |
|---|---|---|---|
| 4,096,164 | 6/1978 | Ellgen et al. | 568/902 |
| 4,304,946 | 12/1981 | Isogsi et al. | 568/902 |
| 4,309,314 | 1/1982 | Hargis et al. | 568/902 |
| 4,405,815 | 9/1983 | Keim et al. | 568/902 |
| 4,476,334 | 10/1984 | Chen et al. | 568/902 |
| 4,625,049 | 11/1986 | Current | 568/902 |
| 4,628,113 | 12/1986 | Current | 568/902 |
| 4,670,473 | 6/1987 | Walker et al. | 518/706 |

Primary Examiner—J. E. Evans
Attorney, Agent, or Firm—Charles J. Enright

[57] ABSTRACT

A process for forming an alcohol fraction boiling in the range of motor gasoline that is enriched in higher alcohols, comprises contacting a mixture of hydrogen, carbon monoxide and a lower alkanol with a catalyst comprising:

(1) a first component comprising molybdenum, tungsten or a mixture thereof in free or combined form;
(2) a second component comprising an alkali or alkaline earth element or a mixture thereof in free or combined form;
(3) an optional third component comprising cobalt, nickel or iron or a mixture thereof in free or combined form; and
(4) an optional fourth component comprising a support, under conditions sufficient to convert at least some of the one or more lower alcohols to higher alcohols.

10 Claims, No Drawings

PREPARATION OF ETHANOL AND HIGHER ALCOHOLS FROM LOWER CARBON NUMBER ALCOHOLS

CROSS-REFERENCE TO RELATED APPLICATION

This is a continuation of application Ser. No. 668,598 filed Nov. 5, 1984, now abandoned.

FIELD OF THE INVENTION

This invention relates to a process for making ethanol and higher alcohols from alcohols with lower carbon numbers.

BACKGROUND OF THE INVENTION

There are several significant processes for making mixed alcohols from synthesis gas or $H_2/CO$. For example, British patent publication No. 2,083,469 discloses such a process wherein the catalyst is based on chromium, zinc and at least one alkali metal. While the applicants claim that the mixed alcohols may contain from 35 to 75 weight percent methanol, the examples given vary from 43 to 69 percent methanol.

The Dow Chemical Company in U.S. Ser. No. 622,029, filed June 18, 1984, now abandoned which is a continuation-in-part of Ser. No. 476,674 which was filed March 18, 1983, now abandoned, both of which are hereby incorporated by reference, and PCT application 84.00405 filed Mar. 16, 1984 published Sept. 27, 1984 as 84/03696 which is also incorporated herein by reference, discloses a process for making mixed alcohols from synthesis gas using a molybdenum-based catalyst.

Substantial methanol may be coproduced with the higher alcohols in these processes. The coproduction of methanol may be undesirable for a number of reasons. At the time this application is being filed, methanol prices are depressed due to oversupply and it is available for a price substantially lower than any of the higher alcohols.

The major targeted use for the synthesized mixed alcohols is as a fuel additive in gasoline engines. Some have held that methanol is an undesirable component for a number of reasons. When blended in hydrocarbon gasolines, methanol is said to increase evaporative emissions and to be liable to phase separation which may lead to corrosion of fuel systems and engine components and possible inferior drivability. While these deficiencies may be in dispute, it is at least desirable to minimize or at least reduce coproduced methanol.

One remedy is to make a lower percentage of methanol in the mixed alcohols. U.S. Ser. No. 635,999, filed July 30, 1984, now abandoned, which is incorporated herein by reference, discloses that one may vary the ratio of methanol to higher alcohols in a mixed alcohols process using a molybdenum-based catalyst by adjusting the concentration of a sulfur-releasing substance in the feed. As the concentration of the sulfur-releasing substance is adjusted upwards, the percentage of methanol in the mixed alcohols produced is lowered. However, in addition, as the sulfur concentration of the feed is increased, the catalyst becomes less active for making alcohols. The minimum practically obtainable weight percentage of methanol in the mixed alcohols at the time of this filing is about 30 percent by this method.

One may also lower the percentage of methanol in the mixed alcohols through catalyst selection. In U.S. Ser. No. 636,000, filed July 30, 1984, now abandoned, which is hereby incorporated by reference, the applicant discloses a catalyst which comprises a first component which may be molybdenum or tungsten, a second component which may be iron, cobalt or nickel, a third component comprising an alkali or alkaline earth element with an optional fourth component being a support. Within certain limits as one increases the ratio of the second component to the first component, the percentage of methanol in the mixed alcohols decreases. One may achieve a methanol content as low as about 10 weight percent at practical productivities using the disclosed catalyst.

It would be desirable to make a lower methanol to higher alcohols ratio at a high productivity and without lowering the activity or selectivity of the catalyst to mixed alcohols.

OBJECTS OF THE INVENTION

It is an object of this invention to make a $C_2$-$C_6$ alcohol from a lower carbon number alcohol. It is a preferred object of this invention to make a mixed alcohols stream with a lower methanol to higher alcohols ratio. It is a more preferred object of the invention to make a mixed alcohol stream with less than 50 weight percent methanol while retaining high activity and selectivity to mixed alcohols. It is an alternative object of this invention to convert lower value methanol into higher valued higher alcohols.

SUMMARY OF THE INVENTION

These and other objects of the invention may be achieved by a process comprising contacting a mixture of hydrogen, carbon monoxide and one or more lower alcohols with a heterogeneous catalyst comprising:
(1) a first component comprising molybdenum, tungsten or a mixture thereof in free or combined form;
(2) a second component comprising an alkali or alkaline earth element or a mixture thereof in free or combined form;
(3) an optional third component comprising cobalt, nickel or iron or a mixture thereof in free or combined form; and
(4) an optional fourth component comprising a support; under conditions sufficient to convert at least part of the one or more lower alcohols to higher alcohols.

It is a feature of this invention that methanol or another lower alcohol is combined with the $H_2/CO$ feed. The advantage of the invention is that the lower value methanol or other alcohols are apparently converted to a higher homologue. While the process appears to be a homologation, the applicants do not wish to be limited to the possibility of this mechanism since the exact mechanism is uncertain.

DETAILED DESCRIPTION OF THE INVENTION

The hydrogen and carbon monoxide required for this process may be obtained by methods known in the art. Examples are gasification of hydrocarbonaceous materials such as coal, high specific gravity oil, or natural gas; as a by-product of partial combustion cracking of hydrocarbons; by steam reforming of liquid or gaseous hydrocarbons; through the water-gas shift reaction; or some combination of these. The two components may also be generated separately and combined for the subject reaction. The molar ratio of hydrogen to carbon monoxide in the feed gas which contacts the catalyst ranges generally from about 0.25 to about 100, preferably from about 0.5 to about 5, and more preferably from about 0.7 to about 3. A most preferred range is from about 0.7 to about 1.5.

The one or more lower alcohols are preferably $C_1$-$C_5$ alcohols. Exemplary alcohols include: aliphatic alcohols such as methanol, ethanol, 1-propanol, 2-propanol, n-butanol, 2-butanol, 2-methyl-2-propanol, and higher homologues; dihydroxy alcohols such as ethylene glycol, propylene glycol and 1,4-dihydroxybutane; trihydroxy alcohols such as glycerine; cycloaliphatic alcohols such as cyclohexanol and substituted cyclohexanols, and phenols and substituted phenols. The lower alcohols may be substituted. Preferably, the substituents are inert. By inert it is meant that the substituent is not altered under the conditions experienced by the lower alcohol during the reaction.

Preferred lower alcohols are the $C_1$-$C_3$ alcohols. Methanol is most preferred because its higher homologues are substantially more valuable. A particularly preferred lower alcohol is one formed by fractionating the mixed alcohol product of the process to remove the methanol which is then recycled back into the feed. One may substantially reduce the methanol content of the mixed alcohols using this scheme or may if one wishes recycle the methanol to extinction. Alternatively, one may bring in methanol from outside the process to add to the feed. This may not decrease the ratio of methanol to higher alcohols in the product but instead may act to upgrade the purchased methanol feed.

The first component of the catalyst preferably consists essentially of at least one member selected from the group consisting of molybdenum and tungsten in free or combined form. Molybdenum is preferred.

The molybdenum or tungsten may be present in the catalyst in "free or combined form" which means that it may be present as a metal, an alloy or a compound of the element. Representative compounds include the sulfides, carbides, oxides, halides, nitrides, borides, salicylides, oxyhalides, carboxylates such as acetates, acetylacetonates, oxalates, etc., carbonyls and the like. Representative compounds also include the elements in anionic form such as molybdates, phosphomolybdates, tungstates, phosphotungstates, and the like and include the alkali, alkaline earth, rare earth and actinide series of salts of these anions. The sulfides, carbonyls, carbides and oxides are preferred, with the sulfides being most preferred.

The second component of th catalyst preferably consists essentially of at least one member selected from the group consisting of the alkali elements or alkaline earth elements in free or combined form. Alkali elements include lithium, sodium, potassium, rubidium and cesium. Alkaline earth elements include magnesium, calcium, strontium and barium. Alkali elements and in particular cesium and potassium are preferred. Potassium is most preferred.

The second component or promoter may be present in free or combined form as a metal, oxide, hydroxide, sulfide or as a salt or a combination of these. The alkaline promoter is preferably present at a level sufficient to render the catalyst neutral or basic.

The second component may be added as an ingredient to the molybdenum or tungsten component or to the support or may be a part of one of the other components such as sodium or potassium molybdate or as an integral part of the support. For example, carbon supports prepared from coconut shells often contain small amounts of alkali metal oxides or hydroxides or the support may contain a substantial amount of the promoter such as when the support is magnesia.

The third optional component of the catalyst preferably consists essentially of at least one element selected from the group consisting of iron, cobalt or nickel in free or combined form. Cobalt and nickel are preferred.

Representative compounds include the sulfides, carbides, oxides, halides, nitrides, borides, salicylides, oxyhalides, carboxylates such as acetates, acetylacetonates, oxalates, etc., carbonyls and the like. Representative compounds also include the elements combined with first component elements in the anionic form such as iron, cobalt or nickel molybdates, phosphomolybdates, tungstates, phosphotungstates and the like. The sulfides, carbonyls, carbides and oxides are preferred with the sulfides being most preferred.

A fourth optional component of the catalyst may be a support which may assume any physical form such as a powder, pellets, granules, beads, extrudates, etc. The supports may be coprecipitated with the active metal species or the support in powder form may be treated with an active metal species and then used as is or formed into the aforementioned shapes or the support may be formed into the aforementioned shapes and then treated with the active catalytic species.

The first three components may be dispersed on the support by methods known in the art. Examples include: impregnation from solution which may be followed by conversion to the active species, vapor deposition, intimate physical mixing, sulfiding of other first or second component species, precipitation of sulfides in the presence of the support and the like. One or more of these methods may be used.

Exemplary support materials include: the aluminas, basic oxides, silicas, carbons or suitable solid compounds of magnesium, calcium, strontium, barium, scandium, yttrium, lanthanum and the rare earths, titanium, zirconium, hafnium, vanadium, niobium, tantalum, thorium, uranium and zinc. Oxides are exemplary compounds. Preferably, the supports are neutral or basic or may be rendered neutral or basic by addition of the alkaline promoters. The aluminas include the alpha, gamma and eta types, the silicas include for example silica gel, diatomaceous earth and crystalline silicates.

The carbon supports, which are preferred, include activated carbons such as those prepared from coals and coal-like materials, petroleum-derived carbons and animal- and vegetable-derived carbons. Preferably, the carbon support will have a surface area of 1 to 1500 $m^2/g$, more preferably 10 to 1000 $m^2/g$ and most preferably 100 to 500 $m^2/g$, as measured by the BET nitrogen test. Exemplary carbon supports include coconut shell charcoal, coals, petroleum cokes, carbons formed by pyrolyzing materials such as vinylidene chloride polymer beads, coal, petroleum coke, lignite, bones, wood, lignin, nut shells, petroleum residues, charcoals, etc.

For several reasons, the preferred form of the catalyst is the alkalized agglomerated sulfide. Certain forms of cobalt/molybdenum sulfide are more preferred. Most preferred is agglomerated, cobalt/molybdenum sulfide in which the cobalt and molybdenum sulfides are coprecipitated.

Methods for making sulfide catalysts are disclosed generally at pages 23–34 of *Sulfide Catalysts, Their Properties and Applications*, O. Weisser and S. Landa, Pergamon Press, N.Y., 1973, the whole of which is incorporated herein by reference.

Sulfide catalysts may be made by precipitating iron, cobalt or nickel sulfide in the presence of ammonium tetrathiomolybdate or other thiomolybdates or thiotungstates and thereafter thermally treating the mixture to convert the thiomolybdate or thiotungstate salt to the sulfide. Alternatively, one may use the methods disclosed in U.S. Pat. Nos. 4,243,553 and 4,243,554, which are hereby incorporated by reference. Combined first and third component sulfides are available commercially from several catalyst manufacturers.

Cobalt and molybdenum may be impregnated as salts on a support, then calcined to the oxide and then sulfided with hydrogen sulfide as taught in G.B. patent publication No. 2,065,491 which is incorporated herein by reference. A cobalt/molybdenum sulfide may be precipitated directly onto a support, but the unsupported cobalt/molybdenum sulfide is preferred. Other combinations of first and second component sulfides may be similarly made.

An unsupported catalyst preferably has a surface area of at least about 10 m$^2$/g and more preferably more than 20 m$^2$/g as measured by the BET nitrogen surface area test.

The preferred method of making a cobalt/molybdenum sulfide or other first and third component sulfide is by adding solutions of ammonium tetrathiomolybdate or other equivalent salt and a cobalt or nickel salt such as the acetate more or less simultaneously to 30 percent acetic acid. This results in a coprecipitation of cobalt or nickel/molybdenum sulfide. By varying the ratios of cobalt or nickel and molybdenum or other salts in the solutions, one may vary the ratio of cobalt or nickel and molybdenum or other elements in the sulfide catalyst.

The cobalt/molybdenum sulfide or other sulfide may then be separated from the solvent, dried, calcined and blended with a second component promoter such as potassium carbonate and agglomerating agents and/or pelleting lubricants, then pelleted and used as a catalyst in the process. It is preferred to protect such catalysts from oxygen from the time it is made until it is used.

The alkali or alkaline earth second component may be added to the active catalytic elements prior to, during or after the formation of the sulfide by physical mixing or solution impregnation. The active metal sulfide may then be combined with binders such as bentonite clay and/or pelleting lubricants such as Sterotex ® and formed into shapes for use as a catalyst.

The finished catalyst may be used in a fixed bed, moving bed, fluid bed, ebullated bed or a graded fixed bed in which the concentration and/or activity in the catalyst varies from inlet to outlet in similar manner to known catalysts. The catalyst may be used in powder form or may be formed into shapes with or without a binder.

Catalysts of the invention preferably contain less than 25 weight percent based on the total weight of carbon oxide hydrogenation active metals, of other carbon oxide hydrogenation active metals and more preferably less than 20 weight percent and most preferably less than 2 weight percent. The inventive catalyst may be essentially free of other carbon oxide hydrogenating components. By "essentially free" it is meant that the other carbon oxide hydrogenating components do not significantly alter the character or quantity of the alcohol fraction. For example, a significant change would be a 5 percent change in the amount of the alcohol fraction or a 5 percent change in the percentage of any alcohol in the alcohol fraction.

Carbon oxide hydrogenating components present in thus limited quantities or excluded are preferably those that contain chromium, manganese, copper, zinc, ruthenium and rhodium. More preferably, in addition to the above-mentioned components, those that contain halogen such as iodine, rhenium, titanium, vanadium, cerium, thorium, uranium, iridium, palladium, platinum, silver and cadmium are excluded.

Preferably, compounds acting as ligands are also absent. Exemplary ligands which may be limited or excluded include those that are disclosed in U.S. Pat. No. 4,405,815, which is incorporated herein by reference. These are generally polydentate ligands in which the donor atoms are phosphorous, arsenic, antimony or bismuth, though other monodentate and polydentate ligands may also be excluded.

It may be advantageous to use conditions for the reaction which encourage low methanol to higher alcohol ratios in the product stream. Two alternative methods would be the aforementioned use of a sulfur-releasing compound in the feed or the addition of cobalt, nickel or iron to the catalyst. These two schemes generally do not work well when they are combined, so one normally uses one or the other. The conditions under which this reaction occurs are similar to those under which mixed alcohols may b formed directly from the H$_2$/CO synthesis gas. Accordingly, the alcohol conversion and the alcohol synthesis reactions take place simultaneously.

In the normal operating ranges, the higher the pressure at a given temperature, the more selective the alcohols synthesis process will be to alcohols. The minimum contemplated pressure is about 500 psig (3.55 MPa). The preferred minimum is about 750 psig (5.27 MPa) with about 1000 psig (7.00 MPa) being a more preferred minimum. While about 1500 psig (10.4 MPa) to about 4000 psig (27.7 MPa) is the most desirable range, higher pressures may be used and are limited primarily by the cost of high pressure vessels and compressors needed to carry out the higher pressure reactions. The typical maximum is about 10,000 psig (69.1 MPa) with about 5000 psig (34.6 MPa) a more preferred maximum. A most preferred operating pressure is about 3000 psig (20.8 MPa).

The minimum temperature used is governed by productivity considerations of the alcohols synthesis reaction and the fact that at temperatures below about 200° C. volatile metal carbonyls may form. Alcohols may also condense at lower temperatures. Accordingly, the minimum temperature is generally around 200° C. A preferred minimum temperature is 240° C. A maximum temperature is about 400° C. Preferably, the maximum temperature is about 375° C. or less, more preferably 350° C. or less and the most preferred range is from about 240° C. to about 325° C.

The H$_2$/CO gas hourly space velocity (GHSV) is a measure of volume of the hydrogen plus carbon monoxide gas at standard temperature and pressure passing a given volume of catalyst in an hour's time. This may range from about 100 to about 20,000 hr$^{-1}$ and preferably from about 300 to about 5000 hr$^{-1}$. Selectivity to alcohols of the alcohols synthesis process generally increases as the space velocity increases. However, conversions of carbon monoxide and hydrogen decrease as space velocity increases and the selectivity to higher alcohols decreases as space velocity increases.

Preferably, at least a portion of the unconverted hydrogen and carbon monoxide in the product gas from the reaction, more preferably after removal of product alcohols, water and carbon dioxide formed and even more preferably any hydrocarbons formed, may be recycled to the reaction. One may wish to isolate one or more of the alcohols and recycle that also. That is typically done in a separate step wherein the alcohol to be recycled is isolated from the balance of the alcohols. For purposes of this discussion, the amount of recycle is expressed as the recycle ratio which is the ratio of moles of gases in the recycle stream to the moles of gases in the fresh feed stream. A recycle ratio of zero is within the scope of the invention with at least some recycle preferred. A recycle ratio of at least about one is more preferred and at least about 3 is most preferred.

The rate of alcohol fed to the process is generally expressed as liquid hourly space velocity (LHSV) which is defined as the volume of liquid alcohols feed at 0° C. and 760 mm Hg pressure which is vaporized and passes over a catalyst bed in an hour's time ratioed to the volume of the catalyst bed. This feed rate may range from about 0.01 $hr^{-1}$ to about 5 $hr^{-1}$ and preferably from about 0.05 $hr^{-1}$ to about 0.5 $hr^{-1}$. Preferably, there is a substantial excess of syngas to alcohol feed and generally, a ratio of at least 2 moles of hydrogen or carbon monoxide per mole of alcohol in the feed.

The alcohol fraction formed boils in the motor gasoline range. The minimum boiling pure alcohol is methanol at 64.7° C. ASTM D-439 calls for a 225° C. end-point for automotive gasoline. Accordingly, the alcohol may boil in a range from about 60° C. to about 225° C. when distilled by ASTM D-86. Other alcohols may boil outside this range but preferably do not. It is not necessary that the entire liquid product boil in this range, but it is preferred. It is not necessary that the alcohol fraction meet all the distillation specifications for motor gasoline; only that it boil within the broad range of motor gasolines. For example, it need not be within the 50 percent evaporated limits as set by ASTM D-439.

Because two processes are taking place simultaneously, one must look at incremental yields to see the extent to which lower alcohols are being converted to higher alcohols. One process is a Fischer-Tropsch type process wherein $H_2/CO$ are converted directly to mixed alcohols. And in fact, some of these alcohols after they are formed during the course of the process, are converted to higher alcohols within the reactor. The second process comprises the conversion of the lower alkanols which are fed to the process into higher alcohols.

When the alcohol is easily differentiated from the products of the Fischer-Tropsch type alcohol synthesis, differentiation of the two processes is quite simple. For example, when the added alkanol is isopropanol, one need only analyze for homologues of isopropanol in the product to adequately define the yields. However, when the alcohol fed is methanol, for example, one must look at incremental yields, that is, look at the yield structure of the mixed alcohols formed without the addition of methanol and then look at the yield structure when methanol is added in addition to the $H_2/CO$ feed.

Using either of these schemes, preferably at least 25 percent of the alcohol added to the reaction is converted to higher homologues.

Under preferred conditions, the amount of water formed is substantially less than the amount of alcohols formed. Typically, there is less than 20 weight percent and preferably less than 10 weight percent water based on the quantity of alcohol. This water may be removed by known techniques if the alcohol fraction is to be used as a motor fuel additive. If the water content is about 5 weight percent or less based on alcohols, the water may advantageously be removed by absorption on molecular sieves. At higher water contents one may use a water-gas shift drying step as disclosed in British patent publication Nos. 2,076,015 and 2,076,423; and U.S. patent application, Attorney's docket No. 31,805-A, filed on or about Oct. 23, 1984, which is a continuation-in-part of U.S. patent application Ser. No. 508,625, filed June 28, 1983, now abandoned. These references are hereby incorporated herein by reference.

The product mixture, as formed under preferred conditions, contains small portions of other oxygenated compounds besides alcohols. These other compounds may not be deleterious to use in the product, as is, in motor fuels. However, these other oxygenates, generally acetate esters, are formed in higher proportions when alcohols are added to the $H_2/CO$ feed than when they are not.

Preferably, the coproducts formed with the alcohol fraction are primarily gaseous products; that is, $C_1-C_4$ hydrocarbons. Preferably, $C_5+$ hydrocarbons are coproduced at less than about 20 percent $CO_2$-free carbon selectivity, more preferably at less than 10 percent and most preferably at less than 5 percent. Lower amounts of normally liquid hydrocarbons make the normally liquid alcohols easier to separate from by-products.

EXAMPLES

Comparison A and Example 1

Comparison A and Example 1 are conducted using a catalyst comprising molybdenum supported on carbon.

Approximately a cubic foot of Witco MBV 4–6 mesh carbon in the form of 3/16-inch (0.48 cm) extrudates is immersed for 10 minutes at 60° C.–70° C. in a solution containing 155.5 pounds of 22 percent ammonium sulfide, 26 pounds of ammonium heptamolybdate and 6.5 pounds of potassium carbonate. The extrudates are then removed and the excess liquor is drained therefrom. The extrudates are then calcined in nitrogen at 300° C. for four hours. These steps are repeated until the extrudates have absorbed 20 percent molybdenum and 5 percent potassium based on the total weight of the catalyst. After the last impregnation, the calcination temperature is raised to 500° C. The catalyst is then passivated with 2 percent oxygen in nitrogen at a maximum temperature of 70° C.

The catalyst is placed in a ½-inch (1.27 cm) stainless steel tube. Total volume of the catalyst is 30 $cm^3$. The weight of catalyst is 22 g. Premixed carbon monoxide and nitrogen from a cylinder is passed through a molecular sieve bed at ambient temperature to remove iron and other carbonyls. Hydrogen and hydrogen sulfide from cylinders is then mixed with the carbon monoxide and nitrogen and the mixture is compressed to the pressure stated. The nitrogen is added at about a 5 percent level to serve as an internal standard for analytical purposes. Methanol is added as stated using a high pressure liquid pump.

The combined feed gas and methanol stream is then preheated and passed at the stated hourly space velocities through the fixed bed reactor which is maintained at the stated reaction temperatures by an electric furnace.

The reactor product is passed through a pressure letdown valve into a vapor-liquid separator at room temperature. The product gases leaving the separator flow past the gas chromatograph sampling port, through a second pressure letdown valve into a dry ice cooled condenser. Liquid products from the vapor-liquid separator and the condenser are collected, weighed, sampled and analyzed. The data sets given represent the combined analyses of both of these samples. The results of the experiment are shown in Table I.

TABLE I

|  | Comparison A | Example 1 |
|---|---|---|
| Temperature (°C.) | 260 | 260 |
| Pressure | | |
| (psig) | 2500 | 2500 |
| (MPa) | 17.3 | 17.3 |
| $H_2/CO$ GHSV ($hr^{-1}$) | 1870 | 1870 |
| $H_2/CO$ mole ratio | 1.12 | 1.12 |
| $H_2S$ level (ppm)* | 20 | 20 |
| Methanol feed rate (g/hr) | 0 | 5.9 |
| Methanol (g/hr) | 2.42 | 7.76 |
| Ethanol | 0.81 | 1.57 |
| Propanols | 0.15 | 0.27 |
| Butanols | 0.016 | 0.023 |
| Pentanols | — | — |
| Methyl Acetate | 0.0433 | 0.211 |
| Ethyl Acetate | 0.016 | 0.015 |

*vol/vol based on $H_2/CO$

The reaction conditions for Comparison A and Example 1 are identical except that methanol is not fed during Comparison A but is fed during Example 1. The addition of methanol results in an increase in the rate of production of higher alcohols. The large increase in the production of acetate esters suggests that the reaction may proceed through the formation of these acetates.

Comparison B and Example 2

The catalyst used in this example is a coprecipitated molybdenum cobalt sulfide.

Ammonium tetrathiomolybdate $(NH_4)_2MoS_4$ and cobalt acetate, in a mole ratio of molybdenum to cobalt of 2 to 1, are added to 30 percent acetic acid at 50° C. The precipitate is filtered and dried under nitrogen at 120° C. and then calcined for 1 hour at 500° C. in a nitrogen atmosphere. The dry cake is then ground together with potassium carbonate, bentonite clay and Sterotex ® to achieve a weight ratio of 66 weight percent $(CoS/2MoS_2)$, 10 weight percent $K_2CO_3$, 20 weight percent bentonite clay and 4 weight percent Sterotex ®. This mixture is then pelleted at 30,000 psig and the pellets are stored under nitrogen until used.

The reaction system for these examples is the same as that for Comparison A and Example 1. Total volume of catalyst is 30 cm³. The weight of catalyst is 32.7 g. The operating conditions and the results are shown in Table II.

TABLE II

|  | Comparison B | Example 2 |
|---|---|---|
| Temperature (°C.) | 290 | 290 |
| Pressure | | |
| (psig) | 2000 | 2000 |
| (MPa) | 13.8 | 13.8 |
| $H_2/CO$ GHSV ($hr^{-1}$) | 2000 | 2000 |
| $H_2/CO$ mole ratio | 1.05 | 1.05 |
| $H_2S$ level (ppm)* | 30 | 30 |
| Methanol feed rate (g/hr) | 0 | 7.0 |
| Methanol (g/hr) | 1.96 | 2.73 |
| Ethanol | 3.31 | 5.36 |
| Propanols | 1.00 | 1.51 |
| Butanols | 0.24 | 0.38 |
| Pentanols | — | — |
| Methyl Acetate | 0.070 | 0.148 |
| Ethyl Acetate | 0.108 | 0.247 |

*vol/vol based on $H_2/CO$

The reaction conditions for Comparison B and Example 2 are identical except that methanol is not fed during Comparison B but is fed during Example 2. The addition of methanol results in an increase in the production of higher alcohols and again in the increase in production of acetate esters.

Comparison C and Example 3

In additional experiments ethanol is added to the $H_2/CO$ feed.

The catalysts in these two examples are the same as those used in Example 2. The reaction is carried out in the same apparatus as Example 2. The reaction parameters and results are set out in Table III.

TABLE III

|  | Comparison C | Example 3 |
|---|---|---|
| Temperature (°C.) | 289 | 289 |
| Pressure | | |
| (psig) | 2000 | 2000 |
| (MPa) | 13.8 | 13.8 |
| $H_2/CO$ GHSV ($hr^{-1}$) | 3000 | 3000 |
| $H_2/CO$ mole ratio | 1.08 | 1.08 |
| $H_2S$ level (ppm)* | 90 | 90 |
| Ethanol feed rate (g/hr) | 0 | 3.32 |
| Methanol (g/hr) | 1.80 | 1.76 |
| Ethanol | 1.36 | 3.24 |
| Propanols | 0.344 | 0.513 |
| Butanols | 0.083 | 0.061 |
| Pentanols | 0.011 | 0.000 |
| Methyl Acetate | 0.046 | 0.055 |
| Ethyl Acetate | 0.026 | 0.092 |

*vol/vol based on $H_2/CO$

It can be seen that the ethanol is converted to higher alcohols. The conversion is not as efficient as it is for methanol however.

Comparison D and Example 4

Using the same catalyst and reactor setup as Example 2, the reaction with ethanol is carried out again. The reaction conditions and results are as set out in Table IV.

TABLE IV

|  | Comparison D | Example 4 |
|---|---|---|
| Temperature (°C.) | 270 | 270 |
| Pressure | | |
| (psig) | 3000 | 3000 |
| (MPa) | 20.8 | 20.8 |
| $H_2/CO$ GHSV ($hr^{-1}$) | 2000 | 2000 |
| $H_2/CO$ mole ratio | 1.05 | 1.05 |
| $H_2S$ level (ppm)* | 30 | 25 |
| Ethanol feed rate (g/hr) | 0 | 2.21 |
| Methanol (g/hr) | 1.078 | 1.198 |
| Ethanol | 0.612 | 1.762 |
| Propanols | 0.171 | 0.244 |
| Butanols | 0.054 | 0.041 |
| Pentanols | 0.006 | 0.000 |
| Methyl Acetate | 0.064 | 0.081 |
| Ethyl Acetate | 0.027 | 0.090 |

*vol/vol based on $H_2/CO$

Again, the ethanol is apparently converted to higher alcohols.

Comparison E and Example 5

The catalyst used in this example is an unsupported molybdenum disulfide catalyst comprising pelletized 66 percent $MoS_2$ (High Surface Area Special $MoS_2$ obtained from Climax Molybdenum), 20 percent bentonite clay, 10 percent $K_2CO_3$, and 4 percent Sterotex ®.

In Comparison E and Example 5, the reactor consists of a jacketed stainless steel pipe packed with catalyst. The total volume of catalyst is about one cubic foot (0.028 m$^3$). The reactor jacket carries a heat-transfer fluid to remove the heat of reaction. The carbon monoxide feed gas passes through a bed of molecular sieves at room temperature to remove iron and other carbonyls. The hydrogen and carbon monoxide feed gases are then mixed at the ratio stated with 300 ppm hydrogen sulfide. Nitrogen is added to the feed gas at two percent by volume as an internal standard and the mixture is compressed to the pressure stated. Methanol is added. The methanol and feed gas mixture is preheated to the stated reaction temperature and then passed through the fixed-bed reactor at the stated hourly space velocity. The reactor products pass through a water-cooled condenser into a high pressure vapor/liquid separator. The product liquids from the high pressure separator pass through a pressure letdown valve into a low pressure vapor/liquid separator. The product gases leaving the high pressure separator pass through a pressure letdown valve, are combined with the gases from the low pressure separator, and flow past a gas chromatograph sampling point. Liquid products from the low pressure separator are collected in a receiver where they may be sampled and analyzed.

The reactor operating conditions for Comparison E and Example 5 are shown in Table V.

TABLE V

|  | Comparison E | Example 5 |
|---|---|---|
| Temperature (°C.) | 233 | 233 |
| Pressure |  |  |
| (psig) | 1800 | 1800 |
| (MPa) | 12.5 | 12.5 |
| $H_2$/CO GHSV (hr$^{-1}$) | 896 | 888 |
| $H_2$/CO mole ratio | 1.04 | 1.05 |
| $H_2S$ level (ppm)* | 300 | 300 |
| Methanol feed rate (g/hr) | 0 | 766.57 |
| Methanol (g/hr) | 683.51 | 1050.29 |
| Ethanol | 305.31 | 333.66 |
| Propanols | 43.50 | 47.58 |
| Butanols | 7.62 | 9.66 |
| Pentanols | 0 | 0 |
| Methyl Acetate | 24.31 | 51.39 |
| Ethyl Acetate | 5.85 | 6.94 |

*vol/vol based on $H_2$/CO

The addition of methanol results in an increase in the production of higher alcohols and again in an increase in production of acetate esters.

Although the invention has been described in considerable detail, it must be understood that such detail is for the purposes of illustration only and that many variations and modifications can be made by one skilled in the art without departing from the spirit and scope of the invention.

We claim:

1. A process comprising contacting a mixture of hydrogen, carbon monoxide and one or more lower alcohols with a heterogeneous catalyst consisting of:
   (1) a molybdenum metal, sulfide, oxide, carbide or a mixture thereof;
   (2) an alkali or alkaline earth element or a mixture thereof in free or combined form;
   (3) optionally a cobalt, nickel or iron, metal, sulfide, oxide or carbide or a mixture thereof;
   (4) optionally an alumina, silica or carbon support; under conditions sufficient to convert at least some of the one or more lower alcohols to higher alcohols.

2. The process of claim 1 wherein the catalyst contains cobalt or nickel.

3. The process of claim 2 wherein the catalyst contains molybdenum sulfide and cobalt sulfide.

4. The process of claim 3 wherein the catalyst contains unsupported molybdenum/cobalt sulfide.

5. The process of claim 4 wherein the catalyst contains potassium.

6. The process of claim 3 wherein the one or more lower alcohols contain methanol.

7. The process of claim 6 wherein the one or more lower alcohols consists essentially of methanol.

8. The process of claim 6 wherein the one or more lower alcohols contain methanol obtained by fractionating a mixed alcohol product containing methanol and the higher alcohols.

9. The process of claim 3 wherein the hydrogen, carbon monoxide, and one or more alcohols are contacted with the catalyst at a temperature from about 240° C. to about 325° C.

10. A process comprising contacting a mixture of hydrogen and carbon monoxide present in a molar ratio of from about 0.7 to about 1.5 and methanol with a heterogeneous catalyst consisting of an alkalized cobalt/molybdenum sulfide at a temperature of from about 240° C. to about 325° C. and a pressure of from about 1500 psig to about 4000 psig to convert at least 25 percent of the methanol to higher alcohols.

* * * * *